US006717162B1

(12) United States Patent
Jongen

(10) Patent No.: US 6,717,162 B1
(45) Date of Patent: Apr. 6, 2004

(54) METHOD FOR TREATING A TARGET VOLUME WITH A PARTICLE BEAM AND DEVICE IMPLEMENTING SAME

(75) Inventor: Yves Jongen, Louvain-la-Neuve (BE)

(73) Assignee: ION Beam Applications S.A., Louvain-la-Neuve (BE)

(*) Notice: Subject to any disclaimer, the term of this patent is extended or adjusted under 35 U.S.C. 154(b) by 0 days.

(21) Appl. No.: 09/868,754

(22) PCT Filed: Dec. 20, 1999

(86) PCT No.: PCT/BE99/00167
§ 371 (c)(1),
(2), (4) Date: Jun. 21, 2001

(87) PCT Pub. No.: WO00/40064
PCT Pub. Date: Jul. 6, 2000

(30) Foreign Application Priority Data

Dec. 24, 1998 (BE) .............................................. 9800935

(51) Int. Cl.[7] .............................. A61N 5/10; A61N 5/00
(52) U.S. Cl. ................................ 250/505.1; 250/492.3; 250/492.1; 315/502; 378/65
(58) Field of Search ................... 250/505.1, 492.3, 250/492.1; 315/502; 378/65

(56) References Cited

U.S. PATENT DOCUMENTS 4,726,046 A * 2/1988 Nunan ......................... 378/65
5,686,733 A * 11/1997 Fallone et al. ............... 250/591

OTHER PUBLICATIONS

Pedroni et al., "The 200–MeV proton therapy project at the Paul Scherrer Institute: Conceptual design and practical realization," *Med. Phys.* 22 (1) (Jan. 1995).

Kanai et al., "Three–dimensional beam scanning for proton therapy," *Nuclear Instruments and Methods* 214, 491–496 (1983).

Database WPI, XP–002136197, Jul. 30, 1988.

Chu et al., "Instrumentation for treatment of cancer using proton and light–ion beams," *Rev. Sci. Instrum.*, vol. 64, No. 8, pp. 2055–2122 (Aug. 1993).

Kraft et al., "The Darmstadt Program HITAG: heavy ion therapy at GSI," *Hadrontherapy in Oncology*, pp. 217–228 (1994).

* cited by examiner

*Primary Examiner*—Nikita Wells
(74) *Attorney, Agent, or Firm*—Merchant & Gould P.C.

(57) ABSTRACT

The invention concerns a method for treating a target volume with a particle beam, in particular a proton beam, which consists in generating said particle beam using an accelerator and in producing from said beam a narrow spot directed towards the target volume, characterized in that said spot sweeping speed and the particle beam intensity are simultaneously varied.

20 Claims, 1 Drawing Sheet

METHOD FOR TREATING A TARGET VOLUME WITH A PARTICLE BEAM AND DEVICE IMPLEMENTING SAME

FIELD OF THE INVENTION

The present invention relates to a process for treating a target volume with a particle beam, in particular a proton beam.

The present invention also relates to a device for carrying out said process.

The field of application is the proton therapy used in particular for the treatment of cancer, in which it is necessary to provide a process and device for irradiating a target volume constituting the tumor to be treated.

STATE OF THE ART

Radiotherapy is one of the possible ways for treating cancer. It is based on irradiating the patient, more particularly his or her tumor, with ionizing radiation. In the particular case of proton therapy, the radiation is performed using a proton beam. It is the dose of radiation thus delivered to the tumor which is responsible for its destruction.

In this context, it is important for the prescribed dose to be effectively delivered within the target volume defined by the radiotherapist, while at the same time sparing as far as possible the neighbouring healthy tissues and vital organs. This is referred to as the "conformation" of the dose delivered to the target volume. Various methods which may be used for this purpose are known in proton therapy, and are grouped in two categories: "passive" methods and "active" methods.

Whether they are active or passive, these methods have the common aim of manipulating a proton beam produced by a particle accelerator so as to completely cover the target volume in the three dimensions: the "depth" (in the direction of the beam) and, for each depth, the two dimensions defining the plane perpendicular to the beam. In the first case, this will be referred to as "modulation" of the depth, or alternatively modulation of the path of the protons into the matter, whereas, in the second case, this will be referred to as the shaping of the irradiation field in the plane perpendicular to the beam.

Passive methods use an energy degrader to adjust the path of the protons to their maximum value, corresponding to the deepest point in the area to be irradiated, associated with a rotating wheel of variable thickness to achieve modulation of the path (the latter device thus being referred to as path modulator). The combination of these elements with a "path compensator" (or "bolus") and a specific collimator makes it possible to obtain a dose distribution which conforms closely to the distal part of the target volume. However, a major drawback of this method lies in the fact that the healthy tissues downstream of the proximal part outside the target volume are themselves also occasionally subjected to large doses. Furthermore, the need to use a compensator and a collimator which is specific to the patient and to the irradiation angle makes the procedure cumbersome and increases its cost.

Moreover, in order to broaden the narrow beams delivered by the accelerator and the beam transport system, so as to cover the large treatment areas required in radiotherapy, these methods generally use a system composed of a double diffuser. However, the protons lose energy in these diffusers, and large irradiation fields at the greatest depths are therefore difficult to obtain unless an "energy reserve" is rendered available by using an accelerator which delivers protons, the energy of which is much higher than that required to reach the deepest areas inside the human body. Now, it is well known that the cost of such accelerators capable of supplying protons increases proportionately with the energy. Despite these drawbacks, passive methods have been widely used in the past and are still widely used today. An example of a passive method which may be mentioned is the "double diffusion" method which is well known in the prior art.

The aim of "active" methods is to solve some, or occasionally even all, of the problems associated with passive methods. In point of fact, there are several types of active methods. A first series of active methods uses a pair of magnets to scan the beam over a circular or rectangular area. This is the case, for example, of the methods known as "wobbling" and "raster scanning". According to some of these methods, the scanned beam is modulated by a path modulator similar to those used in the passive methods. Fixed collimators and path compensators are again used in this case. According to other methods, the volume to be treated is cut into several successive slices, corresponding to successive depths. Each slice is then scanned by the beam, with the aid of the two scanning magnets, so as to cover an area, the contours of which are adapted to the shape of the tumor to be treated. This shape may be different for each of the slices to be treated and is defined using a variable collimator composed of a plurality of movable slides. An example of this type of method is known from W. Chu, B. Ludewigt and T. Renner (*Rev. Sci. Instr.* 64, pp. 2055 (1993)). By means of these methods, large irradiation fields may be treated, even at the deepest points of the volume to be treated. However, according to certain embodiments based on these methods, it is occasionally still necessary to use a bolus and a compensator. In the case of methods which involve cutting into slices, a better conformation is obtained between the dose delivered and the volume to be treated, for each slice. However, it is necessary, for each irradiation slice, to adapt the multi-slide collimator to the contour of the cross section of the volume to be treated. Needless to say, the quality of the conformation will depend on the "fineness" of the cutting into slices.

In order to dispense with the need to use compensators and collimators, even multi-slide collimators, and to obtain the best possible conformation of the dose delivered to the volume to be treated, a second series of active methods uses scanning magnets to define the contour of the area to be irradiated, for each irradiation plane, and performs three-dimensional cutting of the volume to be treated into a plurality of points. As with the first family of active methods, the movement of the beam along the longitudinal dimension, in the direction of the beam, will take place either by modifying the energy in the accelerator, or by using an energy degrader. Said degrader may be located at the accelerator exit or, on the contrary, in the irradiation head, close to the patient. After cutting the volume to be irradiated into numerous small volumes ("voxels"), each of these volumes is delivered the desired dose using a fine beam scanned in the three dimensions. The specific collimators and other compensators are no longer necessary. An example of implementation of this principle is known from E. Pedroni et al. (*Med. Phys.* 22(1) (1995)). According to this embodiment, the dose is applied by scanning, in the three dimensions, a "spot" produced by a narrow beam. This technique is known as "pencil beam scanning" The superposition of a very large number of these individual dose elements, delivered statically, makes it possible to obtain a perfect conformation of the dose to the target volume. According to this embodiment, the change in the position of the spot is always made with the beam switched off. The fastest movement of the spot is made using a deflector magnet (the "sweeper magnet"). The movement along the second scanning axis is made using a degrader ("range shifter"), located in the irradiation head, which allows the spot to be scanned depthwise. Finally, the third direction is covered by means of the movement of the table on which the patient is supported. The position and dose corresponding to each spot are predetermined using a computing system for planning the treatment. During each movement of the beam, that is to say each time the spot is moved, the beam is interrupted. This is done using a magnet having as purpose to divert the beam in a direction other than that of the treatment ("fast kicker magnet").

This embodiment of the "active" methods provides a solution to the problems encountered by the other techniques mentioned above, and makes it possible to obtain the best possible conformation of the dose delivered to the volume to be treated. However, it also suffers from a number of drawbacks. Firstly, the need to interrupt the beam before each change of position of the spot has the consequence of considerably prolonging the duration of the treatment. Next, the movement of the table on which the patient is located is generally considered unsuitable by radiotherapists, who prefer to avoid any action which may have the consequence of moving the organs inside the patient's body. Finally, the use of the degrader ("range shifter") downstream, just before the patient, has the effect of deteriorating some of the characteristics of the beam.

Another example of the implementation of an active method, developed particularly for heavy ion beams, is also known from G. Kraft et al. (*Hadrontherapy in Oncology*, U. Amaldi and B. Larsson, editors, Elsevier Science (1994)). In this case also, the volume to be treated is cut into a series of successive slices. According to this embodiment, to proceed from one slice to another, the depthwise scanning of the spot is carried out by changing the energy of the beam directly in the accelerator, which in this case is a synchrotron. Each slice of the volume to be treated is covered only once by the spot, this spot being scanned using two scanning magnets, in the X and Y directions (the Z direction being that of the beam, in the direction of the depth). The scanning is carried out without interruption of the beam, at constant intensity. The scanning speed is variable and is set as a function of the dose to be delivered to each volume element. It is also adjusted so as to take account of any potential fluctuations in the intensity of the beam. Thus, this method makes it possible to overcome most of the drawbacks associated with the methods described above. However, this method has been specially developed for heavy ions produced by a synchrotron, the energy of which may be varied "pulse by pulse". Furthermore, this system irradiates only once each slice of the volume to be treated, which may pose problems in the event of movement of organs during irradiation (for example when the target volume is affected by the breathing).

The document "Three-dimensional Beam Scanning for Proton Therapy" by Kanai et al. published in Nuclear Instruments and Methods in Physic Research (Sep. 1, 1983), The Netherlands, Vol. 214, No. 23, pp. 491–496, discloses the use of a synchrotron producing a proton beam controlled by scanning magnets, which is then directed towards an energy degrader, the purpose of which is to modify the energy characteristics of the proton beam. This degrader substantially consists of a block of material having a thickness that is discretely variable. The dose of protons for each target volume is adjusted dynamically by means of real-time measurement and calculation which are performed by a computer. This makes it possible to obtain a conformation of the dose to be supplied as a function of the volume of the target. It is observed that no adjustment of the current of the beam is made in the process.

Aims of the Invention

The present invention aims to provide a process and a device for treating a target volume with a particle beam, which avoid the drawbacks of the methods described previously, while at the same time making it possible to deliver a dose to the target volume with the greatest possible flexibility.

In particular, the present invention aims to provide a treatment process and a treatment device which make it possible to obtain a ratio ranging from 1 to 500 for the dose supplied for each element of a target volume.

The present invention aims in particular to provide a process and a device which dispense with a large number of auxiliary elements such as collimators, compensators, diffusers or even path modulators.

The present invention aims also to provide a process and a device which make it possible to dispense with moving the patient.

The present invention aims also to provide a process and a device which make it possible to obtain protection against an absence of emission of the beam (blank or hole) or against an interruption of the movement of said beam.

Characteristic Elements of the Present Invention

A first object of the present invention relates to a process for treating a particle beam produced by an accelerator and devoted to the irradiation of a target volume consisting of for example a tumor to be treated in the case of a cancer, wherein this particle beam is produced using said accelerator, and a spot located in the target volume is formed from this beam, characterised in that the movement of said spot along the three dimensions within the target volume and the variation of the intensity of the particle beam are performed simultaneously, so that the dose to be delivered conforms to the target volume.

Preferably, the movement in the two directions perpendicular to the direction of the beam defining an irradiation plane takes place continuously by scanning while varying the speed of said beam.

The movement of the spot within the target volume from one irradiation plane to another is effected by modifying the energy of the particle beam using an energy degrader.

Advantageously, the energy of the particle beam is modified immediately after it is extracted from the accelerator.

More particularly, the movement in the two directions perpendicular to the direction of the beam takes place continuously.

The scanning speed of said spot is controlled by means of scanning magnets. The simultaneous control of said scanning magnets and of the current intensity of the particle beam is optimally planned using an algorithm for planning the trajectories of said particles, combining therewith a high-level regulation loop for real-time correction of said optimal trajectories in order to obtain a better conformation of the dose to the target volume.

It is thus observed that the conformation to the target volume is achieved without the use of variable collimators and solely by an optimal control of the path of movement of said spot. The target volume is cut into several successive planes perpendicular to the direction of the beam, corresponding to successive depths, the depthwise movement of the spot from one plane to another being achieved by modifying the energy of the particle beam.

Preferably, the movements in an irradiation plane are made using two magnets preferably located in the irradiation head. The movement of the spot from one irradiation plane to another is effected by modifying the energy of the particle beam using an energy degrader.

Advantageously, it is observed that the movement of the spot may be effected without interrupting the beam. In addition, the contours of the areas in each irradiation plane are controlled by scanning elements.

The present invention also relates to the treatment device for carrying out the process described above, and which comprises a particle accelerator such as a cyclotron for obtaining a spot directed towards the target volume, combined with scanning means and in particular scanning magnets for obtaining scanning of said spot in the two directions perpendicular to the direction of the spot, and means for obtaining a variation in the intensity of said particle beam.

Preferably, this device also comprises means for obtaining a variation in the energy of said beam in order to obtain a movement of the spot as a function of the depth of the target volume.

This device also comprises detection devices such as ionization chambers and/or diagnostic elements for carrying out measurements in order to check the conformation to the target volume.

Another object of the present invention lies in a process for treating a target volume with a particle beam, in particular a proton beam, derived from a fixed-energy accelerator such as a cyclotron, wherein a narrow spot which is directed towards the target volume is produced from this particle beam and in that the energy of said particle beam is modified immediately after it is extracted from the accelerator where the movement of a spot (100) within the target volume and the variation of the particle beam intensity are performed simultaneously so that the dose to be delivered conforms to the target volume. This makes it possible to treat, in an environment close to the cyclotron, the problems of scattering of the beam, corrected for example using slits, or the problems of straggling corrected directly at the accelerator exit by means of an analysis magnet. This also makes it possible to reduce the number of neutrons produced in the environment close to the patient. In such an embodiment, the movement of the spot within the target volume is along the three dimensions (X, Y, Z), and the variation of the particle beam intensity are performed simultaneously so that the dose to be delivered conforms to the target volume.

DESCRIPTION OF ONE PREFERRED EMBODIMENT OF THE INVENTION

Figure 1:
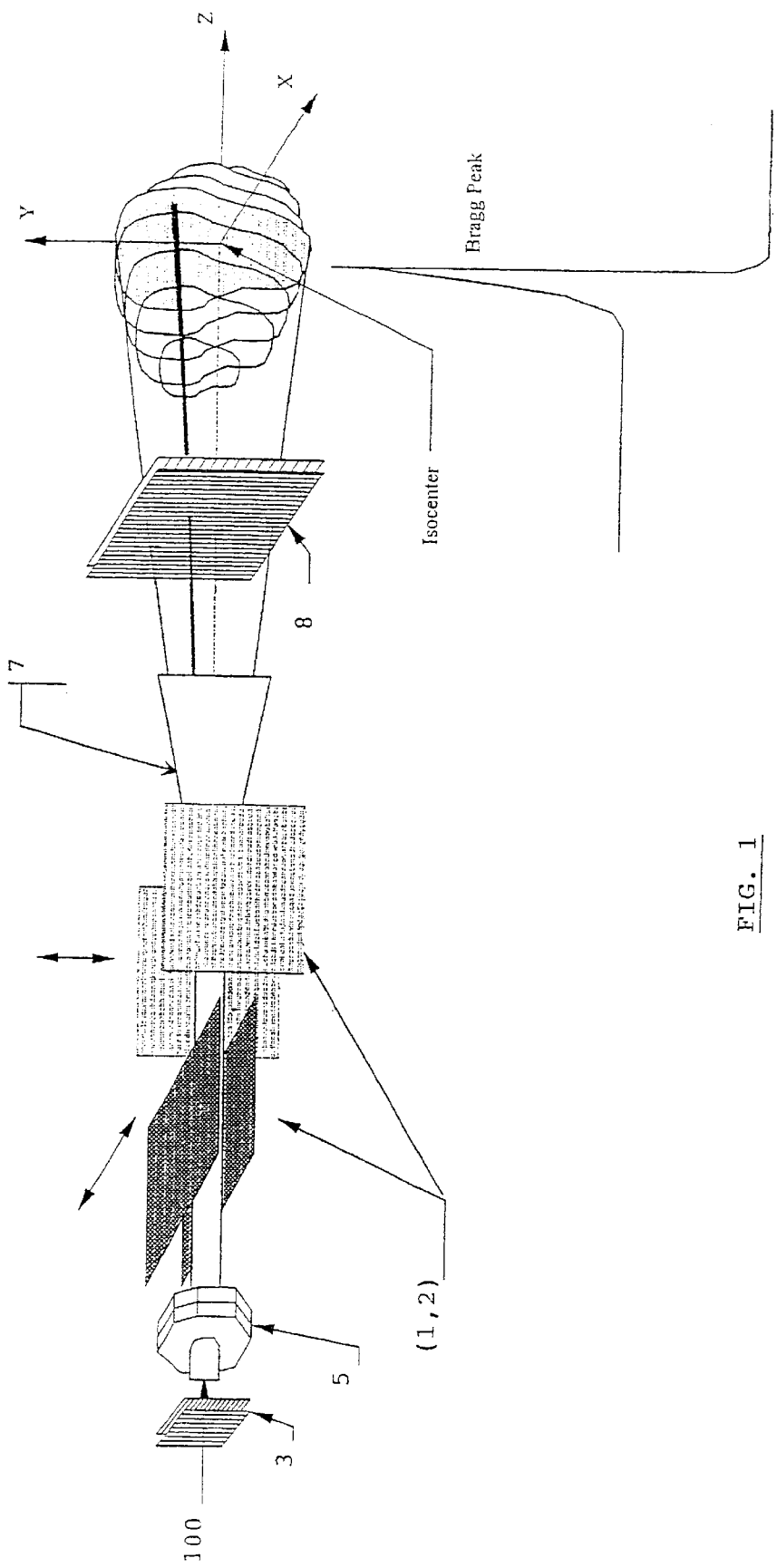
FIG. 1 represents an exploded view of the device for allowing irradiation in order to treat a target volume.

The present invention aims to provide a process and a device for treating a proton beam produced by an accelerator, preferably a fixed-energy accelerator devoted to the irradiation of a target volume consisting, for example, of a tumor to be treated in the case of a cancer, and which have improvements over the prior art described in FIG. 1.

To do this, it is intended to move a spot produced from this proton beam along the three dimensions directly in the patient's body in order to cover the target volume in the three dimensions.

FIG. 1 partially shows the device for carrying out the process according to the present invention. According to one preferred embodiment, a cyclotron (not shown) is used to produce a proton beam 1000 generating a spot 100 to be moved. Means (not shown) are provided for modifying the energy of the proton beam immediately after it is extracted from the accelerator in order to allow the movement of the spot in the longitudinal dimension, that is to say in the direction of the beam, so as to define the various successive irradiation planes Z within the target volume.

Indeed, the target volume 0 is cut into several successive slices corresponding to different depths. Each slice or each irradiation plane is then scanned by said spot, line by line, using the magnets 1 and 2 several times so as to cover an area, the contours of which will be generally different for each slice.

The contours of the areas to be irradiated on each plane are controlled by the scanning magnets 1 and 2. Each of these magnets makes it possible to carry out a scanning either in the X direction or in the X direction.

In order to modify the energy of the emitted beam, an energy degrader is preferably used, and more particularly an energy degrader with characteristics similar to those disclosed by U.S. Pat. No. 6,433,336, having the same assignee.

It is thus observed, in a particularly advantageous manner, that the process and the device according to the present invention do not use elements such as collimators, compensators, diffusers or path modulators, which makes the implementation of said process significantly less cumbersome.

In addition, it is observed that, according to the present invention, no movement of the patient is involved. The irradiation procedure resulting therefrom will be less cumbersome, faster and more accurate. Therefore, it will also be less expensive. Better conformation of the dose delivered to the target volume will thus be obtained, and in a minimum amount of time.

According to one particularly advantageous characteristic, it is observed that the movement of the spot over each irradiation plane takes place without interruption of the beam, which allows a considerable saving in time and reduces the risk of sub-dosing between two consecutive irradiation points.

According to the methodology used, it is envisaged to cover each plane several times in order to limit the dose delivered point by point during each passage, which increases the safety while at the same time limiting the problems due to the movements of the organs inside the body, for instance the breathing.

Preferably, the dose delivered during each passage represents about 2% of the total dose to be delivered.

By envisaging to simultaneously vary the scanning speed of the spot and the intensity of the proton beam, it is possible to obtain an adjustment of the dose to be delivered for each volume element with increased flexibility.

In addition, the safety is also increased in this manner. The reason for this is that any problem associated with an imprecision of one of the two parameters will be automatically corrected by the other.

The methodology used consists in determining the dose corresponding to each spot by predefining the intensity of the beam and the scanning speed for each irradiation volume (or voxel), with the aid of a planning and processing computer system. During the irradiation, dose cards are permanently set up with the aid of measurements carried out by detection devices such as ionization chambers 3, 8 and other diagnostic elements. The intensity of the beam and the scanning speed will be instantaneously recalculated and readjusted so as to ensure that the prescribed dose is effectively delivered to the target volume.

What is claimed is:

1. Process for treating a particle beam (1000) produced by an accelerator in order to irradiate a target volume (0) consisting of for example a tumor to be treated in the case of a cancer, wherein this particle beam (1000) is produced using said accelerator, and a spot (100) located in the target volume is formed from this beam, characterized in that the movement of said spot within the target volume along the three dimensions (X, Y, Z) and the variation of the particle beam intensity are performed simultaneously so that the dose to be delivered conforms to the target volume.

2. Process according to claim 1, characterized in that the movement in the two directions (X, Y) perpendicular to the direction (Z) of the beam defining an irradiation plane takes place continuously by scanning.

3. Process according to claim 2, characterized in that the movement of the spot (100) within the target volume (0) in the two directions (X, Y) perpendicular to the direction (Z) of the beam takes place by varying the scanning speed of said beam.

4. Process according to claim 2, characterized in that the movements in an irradiation plane are effected using two scanning magnets (1 and 2) preferably located in the irradiation head.

5. Process according to claim 4, characterized in that the simultaneous control of the scanning magnets (1 and 2) and of the intensity of the current of the particle beam is performed using an algorithm for planning the trajectories of said particles, combining therewith a regulation loop for real-time correction of said trajectories.

6. Process according to claim 1, characterized in that the target volume is cut into several successive irradiation planes perpendicular to the direction of the beam, corresponding to successive depths, the depthwise movement of the spot from one plane to another being achieved by modifying the energy of the particle beam.

7. Process according to claim 6, characterized in that the energy of the particle beam is modified immediately after extracting it from the accelerator.

8. Process according to claim 1, characterized in that the movement of the spot from one irradiation plane to another is effected by modifying the energy of the particle beam using an energy degrader.

9. Process according to claim 1, characterized in that the movement of the spot is effected without interrupting the beam.

10. Process according to claim 1, characterized in that the contours of the areas in each irradiation plane are controlled by scanning magnets (1 and 2).

11. Process according to claim 1, characterized in that the spot scans each irradiation plane several times.

12. Process according to claim 1, characterized in that the dose corresponding to the spot is defined by predetermining the beam intensity and the scanning speed for each irradiation plane or voxel using a planning and treating data system.

13. Process for treating a cancer tumor afflicting a patient using the process according to claim 1, characterized in that a dose having a conformation corresponding to the volume of the cancer tumor to be treated is delivered to said patient.

14. Device for treating a particle beam produced by an accelerator and devoted to the irradiation of a target volume (0) by a particle beam (1000) according to claim 1, said device comprising a particle accelerator such as a cyclotron for generating a spot (100) located within the target volume (0), combined with scanning means (1 and 2) and in particular scanning magnets for obtaining scanning of said spot in the two directions (X, Y) perpendicular to the direction (Z) of the spot, and means for obtaining a variation in the intensity of said particle beam, characterized in that the scanning means (1, 2) and the means for varying the beam intensity are controlled simultaneously by a planning and regulating algorithm, so that the delivered dose conforms o the target volume.

15. Device according to claim 14, characterized in that it comprises means for obtaining a variation in the energy of said beam in order to obtain a movement of the spot as a function of the depth (Z) of the target volume.

16. Device according to claim 14, characterized in that it comprises at least one detection device such as an ionization chamber (3, 8) and/or a diagnostic element for carrying out measurements in order to verify the conformation of the irradiation dose to the target volume.

17. Device according to claim 14, characterized in that the means for obtaining a variation of the beam energy are located immediately after the extraction of the accelerator.

18. Process for treating a cancer tumor afflicting a patient using the device according to claim 14, characterized in that a dose having a conformation corresponding to the volume of the cancer tumor to be treated is delivered to said patient.

19. Process for treating a particle beam (1000) produced by an accelerator and devoted to the irradiation of a target volume (0) consisting of for example a tumor to be treated in the case of a cancer, wherein the particle beam is produced using a fixed-energy accelerator, and a narrow spot directed towards the target volume is produced from this beam, characterized in that the energy of said particle beam is modified immediately after it is extracted from the accelerator, wherein the movement of a spot (100) within the target volume and the variation of the particle beam intensity are performed simultaneously so that the dose to be delivered conforms to the target volume.

20. Process according to claim 19, wherein the movement of said spot within the target volume is along the three dimensions (X, Y, Z) and the variation of the particle beam intensity are performed simultaneously so that the dose to be delivered conforms to the target volume.

* * * * *